US00PP09634P

United States Patent [19]

Pouw

[11] Patent Number: Plant 9,634

[45] Date of Patent: Aug. 27, 1996

[54] MINIATURE ROSE PLANT NAMED 'RUIKALLA'

[75] Inventor: Antonius A. Pouw, AB Hazerswoude, Netherlands

[73] Assignee: De Ruiter's New Roses, De Kwakel, Netherlands

[21] Appl. No.: 549,953

[22] Filed: Oct. 30, 1995

[51] Int. Cl.[6] ..... A01H 5/00

[52] U.S. Cl. ..... Plt./10

[58] Field of Search ..... Plt./10

*Primary Examiner*—Howard J. Locker

*Attorney, Agent, or Firm*—Proprietary Rights Intl.

[57] ABSTRACT

A distinctive cultivar of miniature rose plant named Ruikalla, characterized by its large red flowers; numerous flowers per plant; rounded bud shape; long shelf-life; and strong rooting habit.

2 Drawing Sheets

The present invention relates to a new and distinct cultivar of the miniature rose class, botanically known as *Rosa hybrida,* and hereinafter referred to by the cultivar name Ruikalla.

The new cultivar is a product of a planned breeding program conducted by the inventor in Hazerswoude, The Netherlands. The objective of the breeding program was to develop compact pot rose varieties with garden performance that can be asexually reproduced by cuttings. The new cultivar originated from a cross made by the inventor in 1991 of two unnamed proprietary seedlings. The cultivar Ruikalla was discovered and selected by the inventor as a flowering plant within the progeny of the stated cross in a controlled environment in Hazerswoude, The Netherlands.

Asexual reproduction of the new cultivar by cuttings taken at Hazerswoude, The Netherlands, has shown that the unique features of this new miniature rose plant are stable and reproduced true to type in successive generations of asexual reproduction.

The following traits have been repeatedly observed and are determined to be the unique characteristics of Ruikalla. These characteristics in combination distinguish the new miniature rose plant as a new and distinct cultivar.

1. Large red flowers.
2. Numerous flowers per plant.
3. Rounded bud shape.
4. Long shelf-life.
5. Strong rooting habit.

The new miniature rose plant has not been observed under all possible environmental conditions. The phenotype may vary significantly with variations in environment such as temperature and light level, without, however, any variance in genotype.

The accompanying colored photographs illustrate typical specimens of the vegetative growth and flowers of the new miniature rose plant, showing the colors as true as it is reasonably possible to obtain in colored reproductions of this type.

The first photograph comprises a top perspective view of a typical plant of the new miniature rose plant grown in Hazerswoude, The Netherlands.

The second photograph comprises details of the new miniature rose plant. In this photograph the top of a young shoot (1); a leaf with three leaflets (2); a leaf with five leaflets (3); a leaf with seven leaflets (4); a stem with prickles (5); a flower bud after sepals open (6); a flower bud after petals begin to unfurl (7); a flower one-third to one-half open (8); a flower fully open (9); a flower stem with sepals, stamens and pistils (10); a flower stem with sepals and pistils (11); a flower stem with pistils only (12); and a spray of five flowers and one flower bud (13) are shown.

The following observations, measurements, values, and comparisons describe plants grown in Hazerswoude, The Netherlands, under glass covering with average day temperature of 20° C., average night temperatures of 16 to 18° C., and an average light level of 2,000 J/cm$^2$.

In the following description, color references are made to The Royal Horticultural Society Colour Chart except where general terms of ordinary dictionary significance are used.

Classification:

*Botanical.*—*Rose hybria* cultivar Rikalla.

*Commercial.*—Miniature pot rose.

Parentage:

*Male or pollen parent.*—Unnamed proprietary seedling.

*Female or seed parent.*—Unnamed proprietary seedling.

Plant description:

*Form.*—Rounded form, uniform, and spreading.

*Growth habit.*—Moderately vigorous, yet compact. Freely banching, dense growth. Suitable for 10-cm containers. Time to produce a finish plant in a 10-cm container 20 to 30 cm in height is generally 10 to 12 weeks depending on average temperature, high level, and cultural practices.

*Stem and lateral branches.*—Quantity of laterl branches from pinching: Generally three. Length of lateral branches: 1 to 5 cm. Color: 143C.

*Foliage description.*—Leaves arranged alternately, compound with three to seven leaflets per leaf, generally symmetrical, abundant, and flat in aspect. Stipules at leaf base. Quantity: Five to eight per lateral branch. Leaflet size: Length: 2 to 2.5 cm. Width: 0.5 to 1 cm. Shape: Ovate with acute tip and obtuse base. Texture: Smooth and leathery. Margin: Serrate. Petiole length: 1.5 to 2 cm. Color: Young foliage, upper side: 137C. Young foliage, under side: 138B with 46B at margin. Mature foliage, upper side: 137A. Mature foliage, under side: 137C. Petiole: 143C. Stipule: 143C. Venation, upper side: 145A. Venation, under side: 145B.

*Prickles.*—Located on petioles and stems. Length: 0.1 to 0.4 cm. Color: 145A.

Flower description:

*Flower type and habit.*—Large red flowers. Consistently symmetrical rosette flowers that are flat in aspect. Freely and continuously flowering. The flowers are borne singly on peduncles and arranged in clusters of up to nine flowers each. These are numerous sprays per plant.

*Flowering season.*—Year-round under greenhouse conditions, optimal flowering during summer and autumn in the Northern Hemisphere.

*Flower diameter.*—3 to 4 cm.

*Flower depth (height).*—1 to 2 cm.

*Flower longevity on plant.*—22 Days.

*Fragrance.*—None.

*Persistent.*—Yes.

*Flower buds.*—Shape; Ovoid, rounded. Size: Length: 1 to 1.5 cm. Width: 0.4 to 0.6 cm. Color: 143B.

*Petals.*—Quantity: At least 35 to 45 per flower. Arrangement: Seven to nine rows of petals with five petals each. Size: Length: 1 to 1.5 cm. Width: 0.6 to 1.2 cm. Shape: Rounded with obtuse tip. Texture: Smooth and satiny. Margin: Entire. Color: When opening: 45A. Upper side, mature: 45B. Under side, mature: 45C. Fade: Upper and under sides fade to 46C and eventually to 47D.

*Petaloids.*—Quantity: At least 20 per flower. Arrangement: Four rows of petals with five petaloids each. Size: Length: 0.1 to 0.7 cm. Width: 0.2 to 0.5 cm. Shape: Elliptical with obtuse tip. Texture: Smooth and satiny. Margin: Entire. Color: Immature: 58C with white at base. Mature: 58B with white at base.

*Sepals.*—Quantity: Five per flower Arrangement: One row with five sepals. Shape: Narrowly ovate with acute tip. Color: Upper side: 137C with 142B at base. Under side: 137C with 142D at base.

*Calyx.*—Almost inconspicuous. Shape: Funnel.

*Peduncles.*—Strong and erect, pubescent. Length: 3 to 4 cm. Color: 143C.

*Reproductive organs.*—Stamens: Quantity: 15 to 30 per flower. Anther size: 0.1 to 0.2 cm. Anther shape: Oblong. Anther color: 159C with 179B. Pistils: Quantity: 5 to 20 per flower. Style length: 0.5 cm. Stigma color: 179B.

Disease resistance: No resistance or susceptibility observed.

Seed production: Seed production is rarely observed.

It is claimed:

1. A new and distinct miniature rose plant named Ruikalla, as illustrated and described.

* * * * *

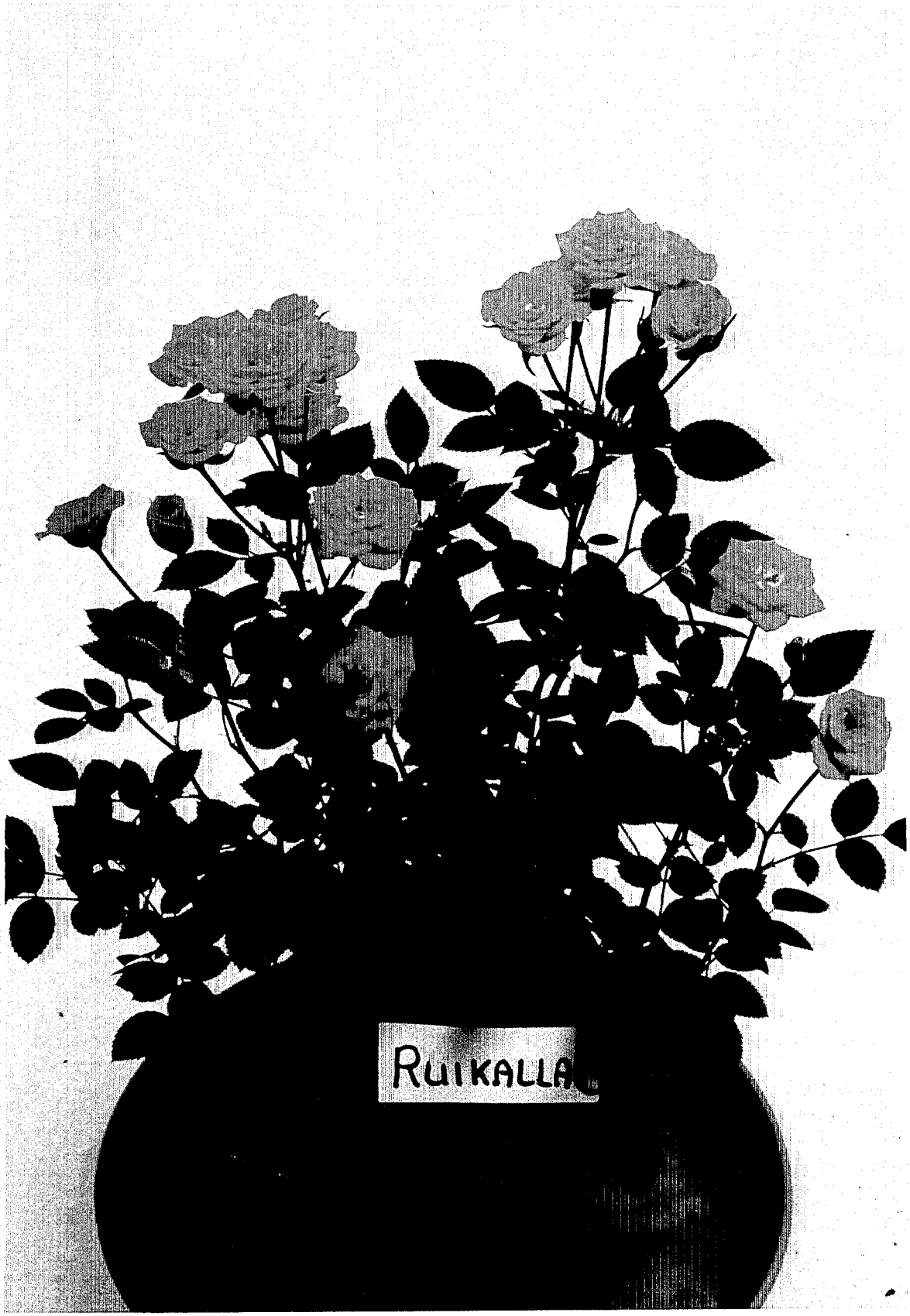
RUIKALLA

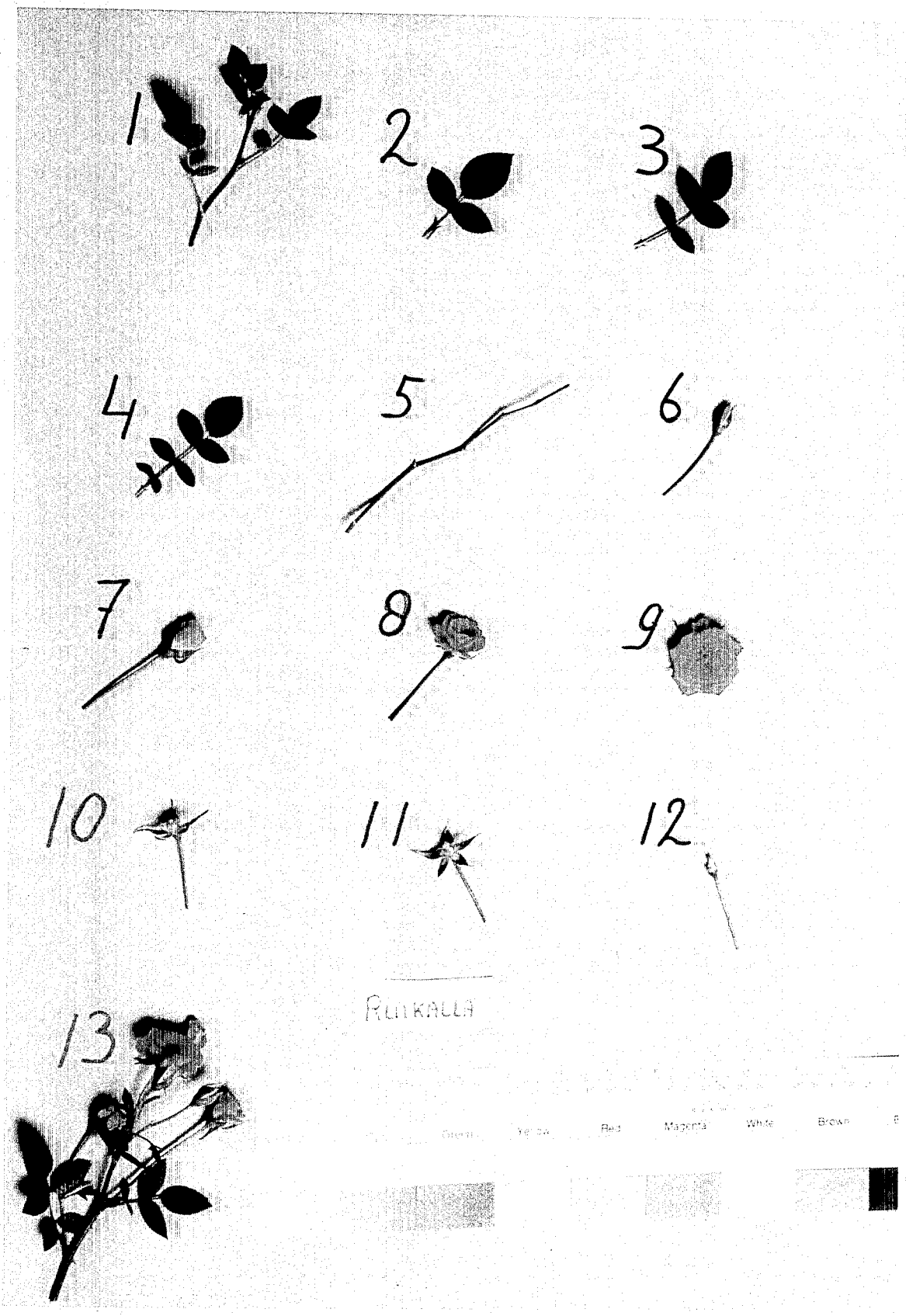
1
2
3
4
5
6
7
8
9
10
11
12
13
RUTKALLA